(12) United States Patent
Rosheim

(10) Patent No.: US 8,197,469 B2
(45) Date of Patent: Jun. 12, 2012

(54) INSERTER JOINT AND INSERTER

(75) Inventor: Mark E. Rosheim, St. Paul, MN (US)

(73) Assignee: Ross-Hime Designs, Inc., Minneapolis, MN (US)

( * ) Notice: Subject to any disclaimer, the term of this patent is extended or adjusted under 35 U.S.C. 154(b) by 1502 days.

(21) Appl. No.: 10/760,898

(22) Filed: Jan. 20, 2004

(65) Prior Publication Data

US 2005/0159732 A1 Jul. 21, 2005

(51) Int. Cl.
*A61B 18/00* (2006.01)

(52) U.S. Cl. .......... 606/1; 606/41; 606/42; 606/45; 606/50; 74/490.01; 74/490.05; 74/490.06; 414/729; 414/735; 607/101; 607/102; 607/115; 607/116; 901/15; 901/28; 901/29

(58) Field of Classification Search .......... 74/490.01, 74/490.05, 490.06; 414/729, 735; 606/1, 606/41, 42, 45–50; 607/101, 102, 115, 116; 901/15, 28, 29

See application file for complete search history.

(56) References Cited

U.S. PATENT DOCUMENTS

| | | | | | |
|---|---|---|---|---|---|
| 4,989,123 | A | * | 1/1991 | Best | 362/102 |
| 5,699,695 | A | * | 12/1997 | Canfield et al. | 74/490.06 |
| 5,979,264 | A | * | 11/1999 | Rosheim | 74/490.06 |
| 6,418,811 | B1 | | 7/2002 | Rosheim | |
| 6,461,356 | B1 | * | 10/2002 | Patterson | 606/41 |
| 6,557,432 | B2 | | 5/2003 | Rosheim | |
| 7,162,309 | B2 | * | 1/2007 | Laske et al. | 607/122 |

\* cited by examiner

*Primary Examiner* — Aaron Roane
(74) *Attorney, Agent, or Firm* — Kinney & Lange, P.A.

(57) ABSTRACT

A controlled relative motion system comprising a base support, a manipulable support, and a plurality of hinged doubled pivoting links rotatably coupled to the base support and rotatably coupled to the manipulable support. A plurality of force imparting members has at least one coupled to one of the plurality of doubled pivoting links so as to be able to cause it to rotate. Also, at least one is coupled to the base support so as to be able to cause that base support to move toward or away. This joint can be used with a similar control joint, coupled thereto by coupling shafts held apart by a slidable separator, to form an extended length inserter for inserting an object positionable by the insertion joint in an obstructed location reached along a constricted passageway. These structures, positioned within a barrel, can rotate together but an activator slider, positioned at least partially about that barrel though not rotatable therewith, is coupled to the separator to cause sliding thereof.

30 Claims, 13 Drawing Sheets

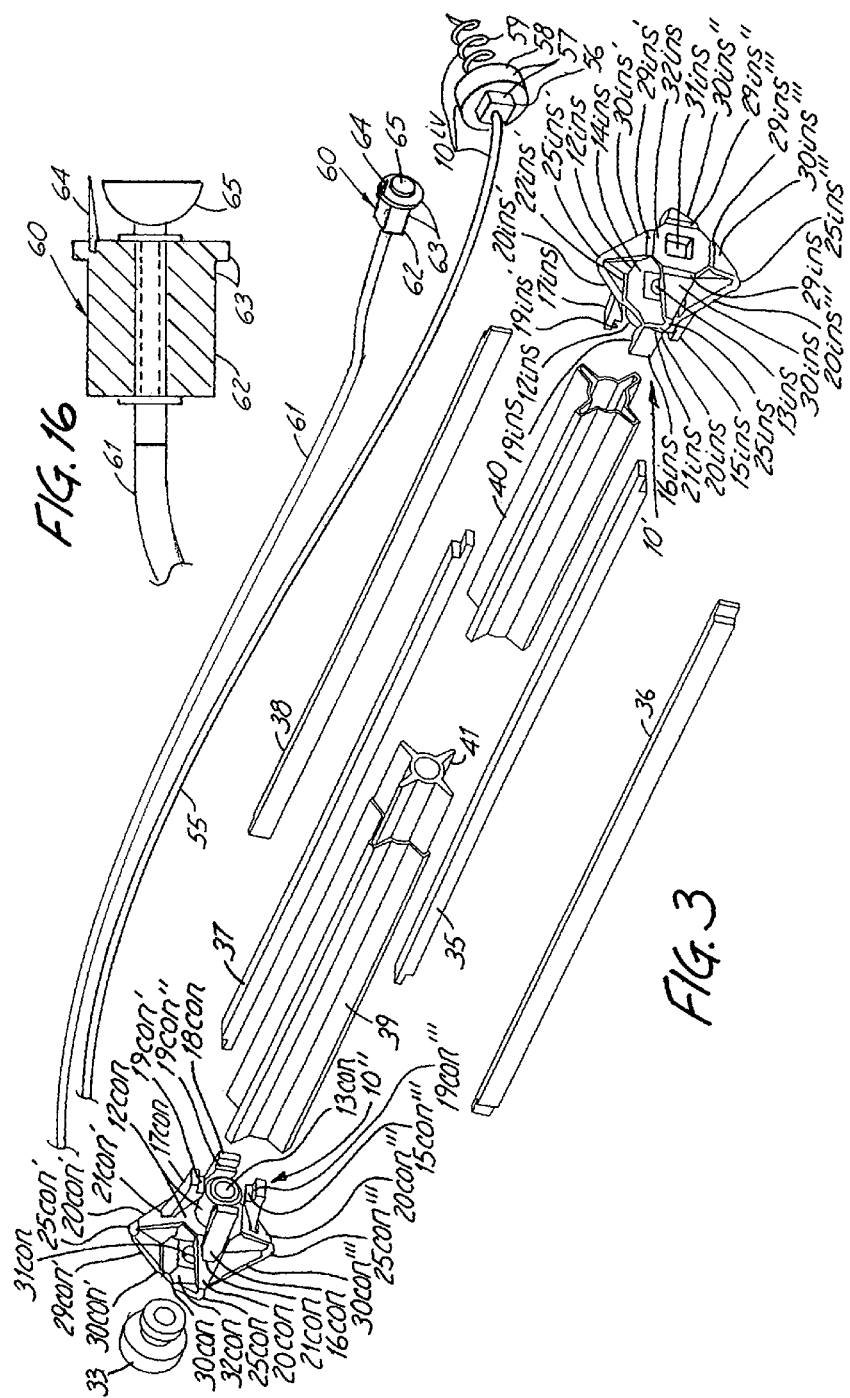

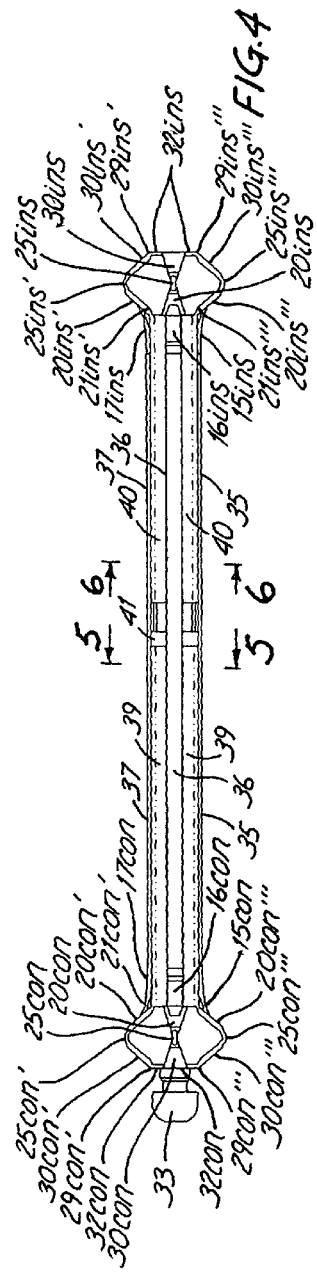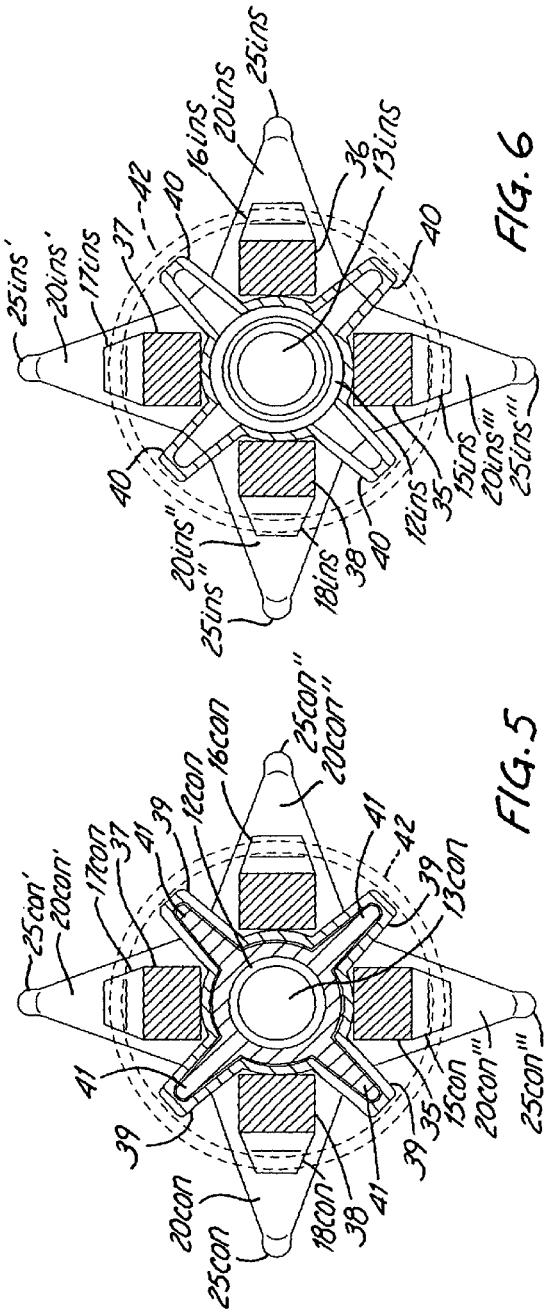

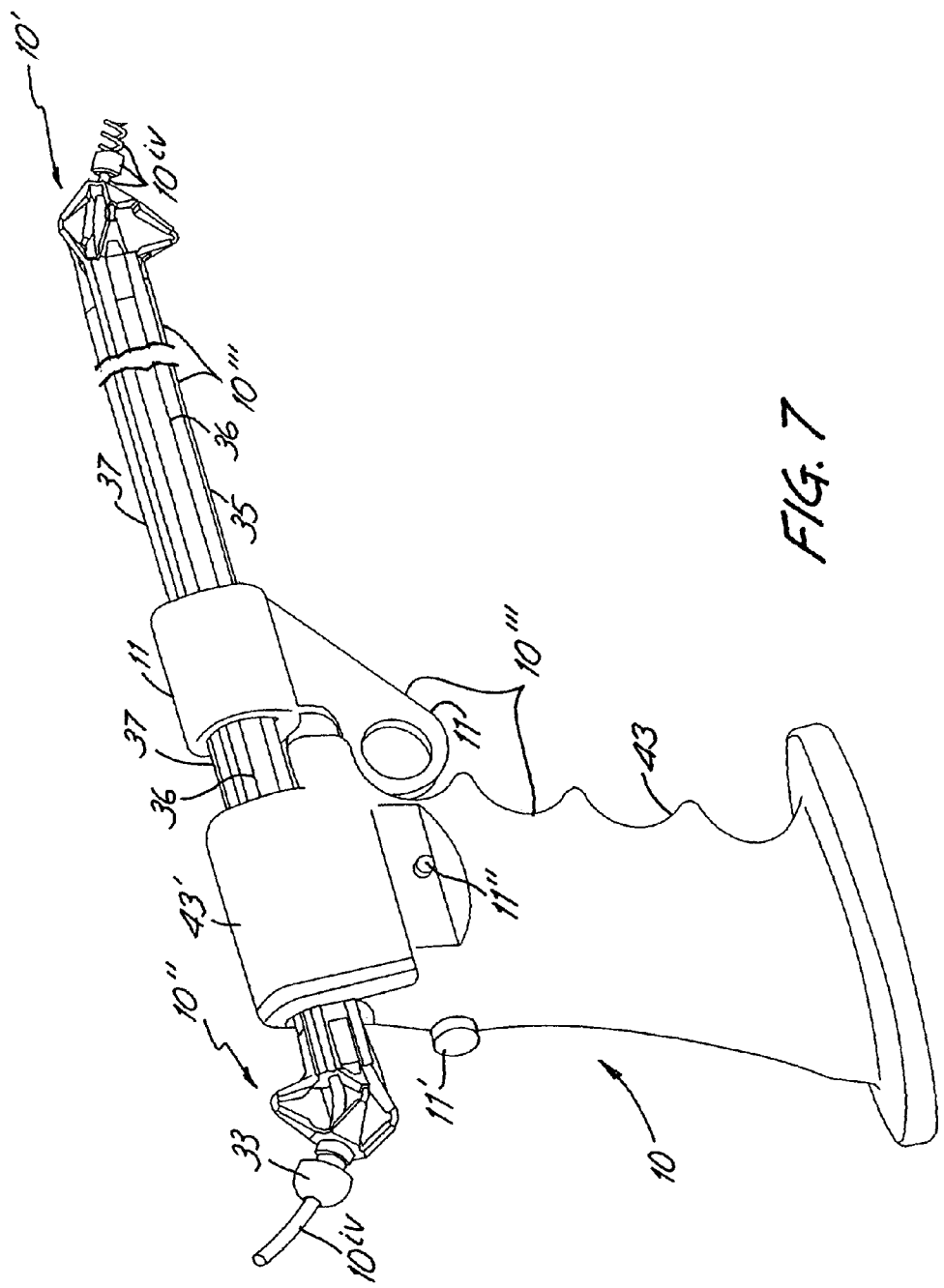

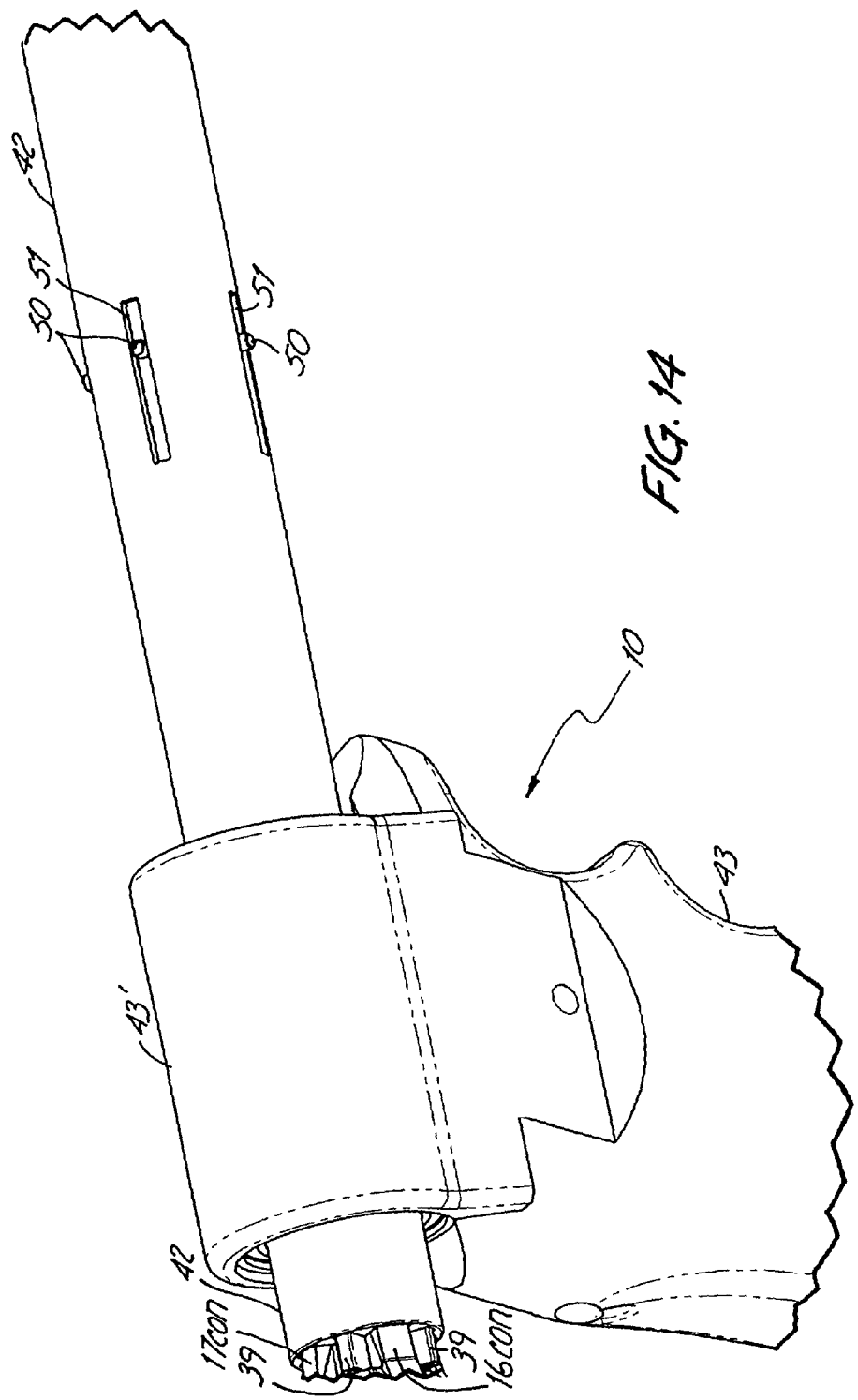

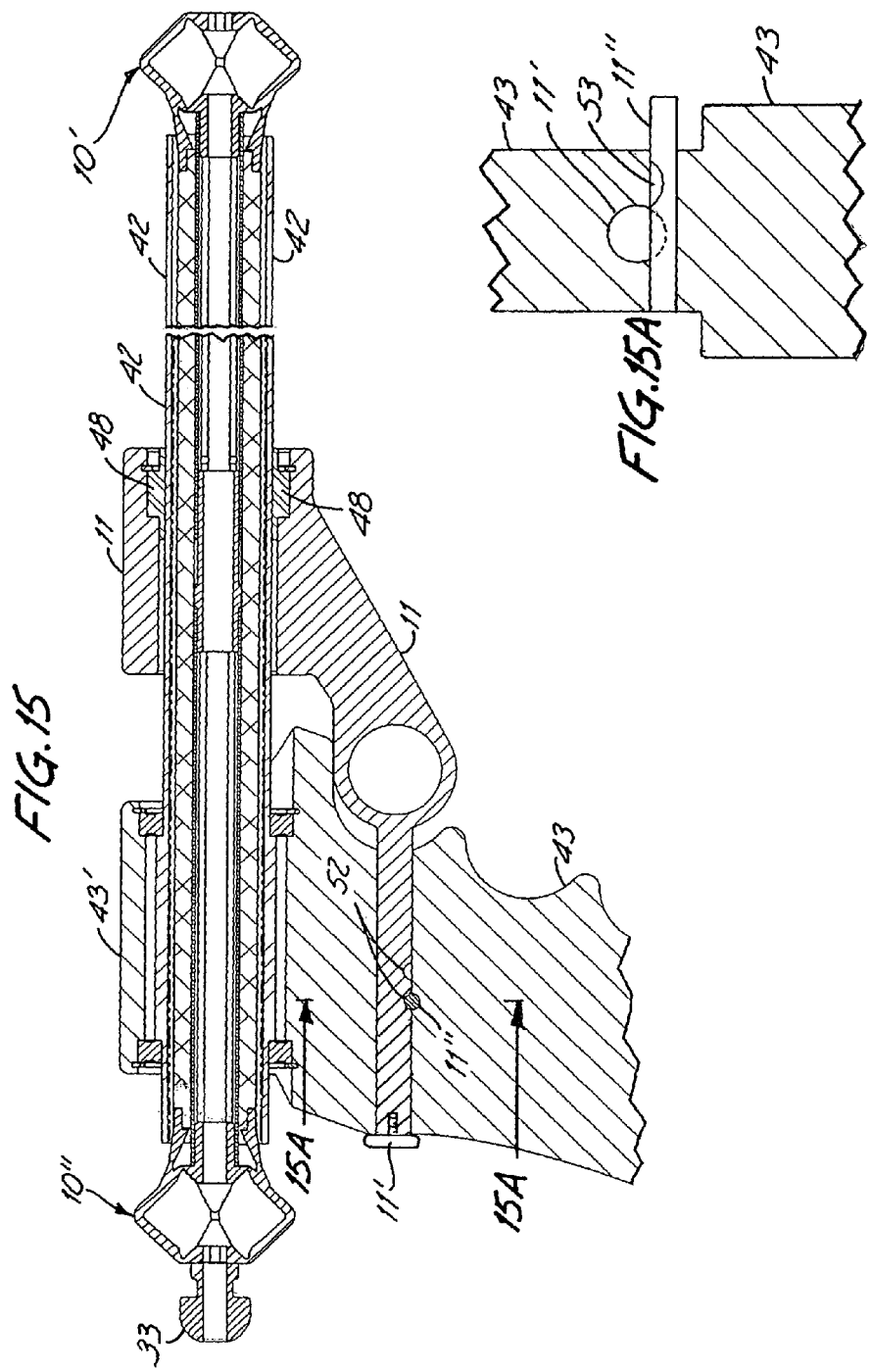

INSERTER JOINT AND INSERTER

BACKGROUND OF THE INVENTION

The present invention relates to robotic manipulators and, more particularly, to robotic manipulators operated relatively remote to the operator.

There is a recurring need for the capability of positioning selected items in selected locations interior to various kinds of entities, and often in situations in which those locations can't be seen, or can't be otherwise reached, or both, during such positioning. Such situations may arise in connection with locations occurring within complicated mechanisms or human or animal bodies, or behind protective barriers or the like.

Of course, in some of these situations there may be the possibility of partially disassembling or opening up the entity in the interior of which the desired item is to be placed. This is often inconvenient or expensive, or both, and leaves the other situations unremedied in which such disassembly or opening is not possible.

An alternative is the use of a robotic manipulator operable at some distance from the operator. One such mechanical manipulator meeting this desire comprises a base support, a manipulable support and a plurality of pivoting links therebetween. The pivoting links are rotatably coupled to both the base support so as to be arrayed by rotational axis thereabout and the manipulable support with a hinge between the rotatably connected ends of these pivoting links. In some embodiments, these components of such manipulators can be partially, or even completely, jointly formed of polymer materials in a common mold. Such systems can incorporate a variety of force imparting members to control movements of various ones of the pivoting links with as few as two being required. Pivoting links having such hinged portions provide a capability for controlling the separation between the base and manipulable supports though requiring an actuator for each pivoting link.

Force imparting members of various kinds can be used with such a robotic manipulator but are often bulky such as linear actuators, motor driven gear trains and the like. Such force imparting members cannot be near the robotic manipulator operating in an entity in which there is little room therein for that robotic manipulator and its operating apparatus if the point of entry into such an entity is relatively far from the location in which the desired item is to be positioned. The use of flexible but stiff wires at the outputs of such linear actuators is a possibility but any bending of them even in a sleeve greatly raises the friction should any subsequent rotation of them be desired. Thus some arrangement is needed, with these force imparting members such as linear actuators, that provides a separation distance between such a linear actuator and the robotic manipulator for those situations in which there is little room in the entity for the robot manipulator and its operating apparatus to maneuver in positioning the desired item without too greatly interfering with operation of the robotic manipulator.

BRIEF SUMMARY OF THE INVENTION

The present invention provides a controlled relative motion system permitting a controlled motion member therein, joined to a base member therein, to selectively move with respect to that base member, and comprises a base support, a manipulable support, and a plurality of doubled pivoting links each having therein a base link and a manipulable link rotatably coupled to one another by a link hinge supported both by the base link and the manipulable link. The base link in each of this plurality of doubled pivoting links is rotatably coupled to the base support by a base hinge supported both by the base link and the base support so as to be rotatable about a corresponding base link axis. The manipulable link in each of the plurality of doubled pivoting links is rotatably coupled to the manipulable support by a manipulable hinge supported both by the manipulable link and the manipulable support so as to be rotatable about a corresponding support link axis. In addition, there is a plurality of force imparting members at least one of which is coupled to a base link in one of the plurality of doubled pivoting links so as to be able to cause that said base link to rotate about its corresponding base link axis. Also, at least one of the plurality of force imparting members is coupled to the base support so as to be able to cause that base support to move toward or away from at least a portion of that force imparting member. These various hinges can be formed from, and joined together by, a common material used in both supporting portions thereof such that the hinge is formed at least in part by a thinned portion of that material extending between the supporting portions.

This joint, as an insertion joint, can be used with a similar control joint, coupled thereto by coupling shafts held apart by a slidable separator, to form an extended length inserter for inserting an object positionable by the insertion joint in an obstructed location reached along a constricted passageway. These structures, positioned within a cylindrical shell like barrel, can rotate together but an activator slider, positioned at least partially about that barrel though not rotatable therewith, is coupled to the separator to cause sliding thereof.

BRIEF DESCRIPTION OF THE DRAWINGS

FIG. 3 is an exploded view of a portion of the embodiment shown in FIGS. 1 and 2, FIG. 4 is an assembled side view of part of that portion of the embodiment shown in FIG. 3, FIGS. 5 and 6 are cross section views of the assembly shown in FIG. 4, FIG. 7 is a perspective view of a partial disassembly of the embodiment shown in FIG. 2 in yet another state, FIG. 14 is a perspective view of a partially disassembled portion of the embodiment shown in FIG. 13, FIG. 15 is a side cross section view similar to that of FIG. 11 but including more of the embodiment shown there, FIG. 15A is a fragmentary cross section view of the embodiment shown in FIG. 15, and FIG. 16 is a cross section side view of a part of that portion of the embodiment shown in FIG. 3.

DETAILED DESCRIPTION

Figure 1:
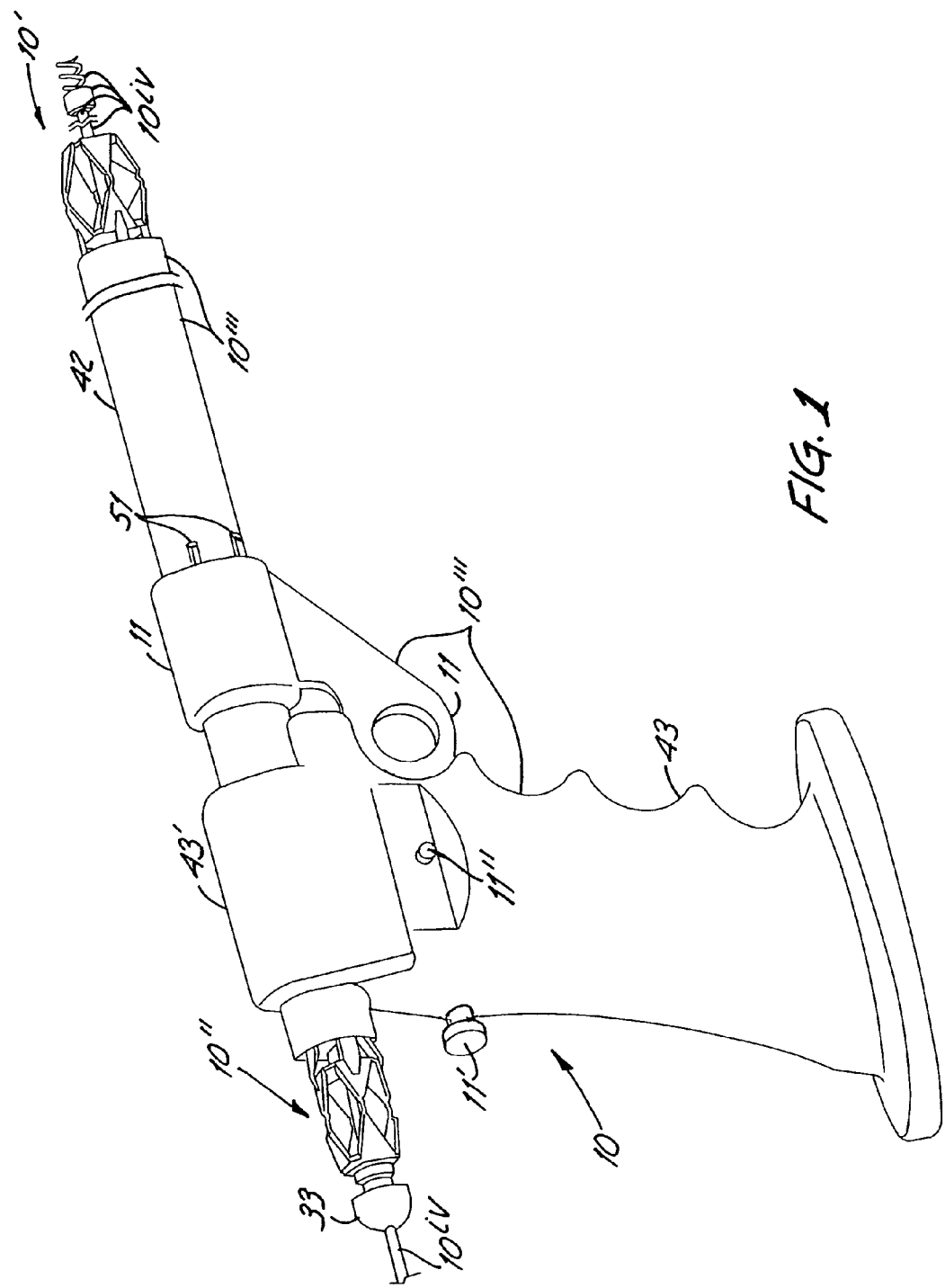
FIG. 1 is a perspective view of an embodiment of the present invention in one state.

An inserter device having the capability of positioning selected items in selected locations interior to various kinds of entities, even in situations in which those locations can't be seen, or can't be otherwise reached, or both, during such positioning is represented in the perspective view thereof shown in FIG. 1. The example shown there and described in the following is an inserter device arrangement, 10, employing a version of the kind of manipulator mentioned above both as an insertion joint, 10', and as an activating control joint, 10", separated by an activatable translation positioner arrangement, 10''', in this inserter device. Inserter device arrangement 10 is for use in positioning, or positioning and attaching, an item held in insertion joint 10' into some entity in which it is positioned by the inserting of the corresponding end of inserter 10 therein to that location, the example shown in FIG. 1 being electrical interconnection lead, $10^{iv}$, for positioning at and attaching to a biological object such as a human heart as might be done in connecting a heart pacemaker thereto.

Activation of positioner 10''' to translate insertion joint 10' between positions available thereto is controlled by a slide barrel, 11, and a push bar, 11', extension thereof which can be locked and unlocked from certain positions available thereto by a lock bar, 11". In FIG. 1, slide barrel 11 and push bar 11' are shown positioned at their farthest possible location to the left so that insertion joint 10' and control joint 10" are, as a result, relatively elongated along the corresponding portions of interconnection lead $10^{iv}$ positioned therein. In this configuration, these joints have a minimal lateral cross sectional extent so that insertion joint 10' can be slid along the interior of a relatively narrow passageway, such as in a human body, with relatively little interference with the passageway side walls, but there is no angular positioning capability for orienting that joint.

Figure 2:
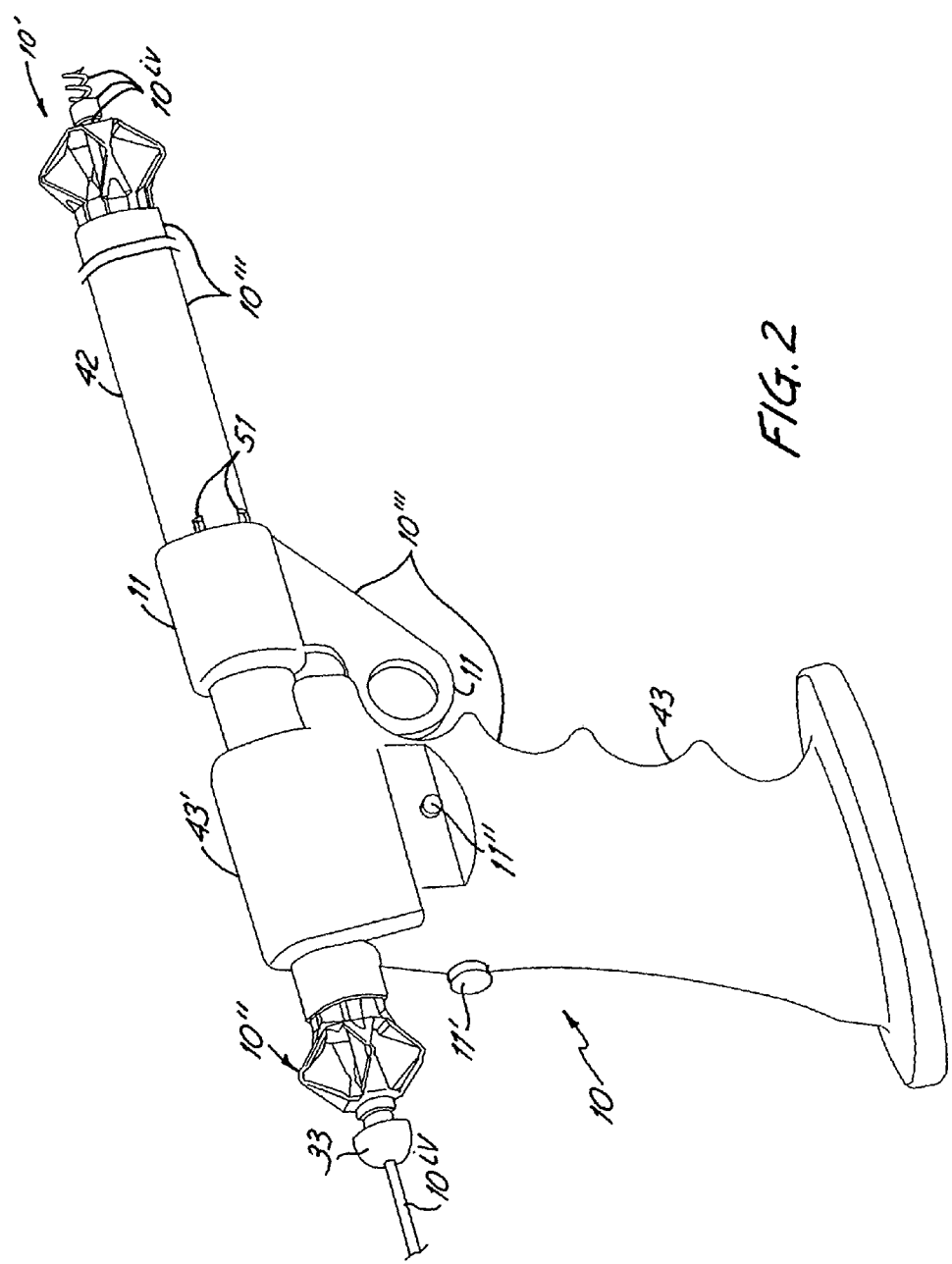
FIG. 2 is a perspective view of an embodiment of the present invention in another state.

Turning next to FIG. 2, slide barrel 11 and a push bar 11' are shown positioned at their farthest possible location to the right so that insertion joint 10' and control joint 10" are thereby relatively shortened along the corresponding portions of interconnection lead $10^{iv}$ positioned therein. In this circumstance, these joints have a maximal lateral cross sectional extent but this configuration is selected only after insertion joint 10' has reached its destination, such as being at the surface of a human heart, so that interference during sliding is generally not occurring. However, this configuration allows an angular positioning capability for orienting insertion joint 10' which can be of aid in directing the proper placement of the end of interconnection lead $10^{iv}$.

These capabilities for configuring and orienting insertion joint 10' are provided through the structures of insertion joint 10' and control joint 10", and by the apparatus provided extending between these joints that is located within positioner 10'''. Much of this apparatus is shown in the exploded view thereof, and of joints 10' and 10", provided in FIG. 3 along with a perspective view of interconnection lead $10^{iv}$ and a further item as an alternative insertable arrangement thereto. Insertion joint 10' and control joint 10" can each be provided formed of molded plastic in a single plastic material injection step in suitable multicavity molds. Polypropylene (possibly having distributed fibers therein) is a typically used structural polymer for forming these joints because of being fairly rigid but bendable and so is the material that is typically is injected into a multicavity mold to form same.

These joints are typically formed also with molded plastic "living hinges" as a part of their molded structure for allowing adjacent structural portions thereof, joined by such "hinges", to rotate with respect to one another to thereby allow providing small, relatively cheap structures for the joints. In a so called "living hinge", the two sides of the hinge are each integral with one of the two corresponding structural members being hinged together to accomplish the affixing of the hinge sides thereto, and the hinge pin in a typical metal hinge is provided here by a thinned portion of the plastic material forming the hinge that is continuously extended between these two corresponding structural members of thicker material rather than by a separate pin joining such members.

Thus, insertion joint 10' is supported on a base, 12ins, formed of a tubular portion extending from the left in FIG. 3 to the right with a passageway, 13ins, through the center thereof opening circularly through a capping plate, 14ins, formed as a center open square with its corners missing on corresponding diagonals thereacross, this plate being affixed to the right end of the tubular portion. Insertion joint 10' has a plurality of force imparting shafts, 15ins, 16ins, 17ins and 18ins (not seen in FIG. 3), each extending from an unconnected end thereof on the left in the figure to the right, and have in each of those unconnected ends a corresponding one of a plurality of notches, 19ins, 19ins', 19ins" and 19ins'". These shafts extend toward the right sufficiently to join a corresponding one of a plurality in inner pivoting links, 20ins, 20ins', 20ins" and 20ins''', through a corresponding one of a plurality of "living hinges", 21ins, 21ins', 21ins" and 21ins''' (not all of these structures can be seen in this view). Force imparting shaft 16ins is used to rotate pivoting link 20ins about a further "living hinge", 22ins, (not seen in FIG. 3) connecting it to base 12ins. In the same manner, force imparting shaft 17ins is used to rotate pivoting link 20ins' about yet a further "living hinge", 22ins', connecting it to base 12ins. Again, force imparting shaft 18ins is used to rotate pivoting link 20ins" about another "living hinge", 22ins", connecting it to base 12ins. Finally, force imparting shaft 15ins is used to rotate pivoting link 20ins''' about yet another "living hinge", 22ins''', that connects that pivoting link to base 12ins.

Inner pivoting links 20ins, 20ins', 20ins" and 20ins''' are connected by a corresponding one of a plurality of linking "living hinges", 25ins, 25ins', 25ins" and 25ins''' to the outer portion of insertion joint 10' having a corresponding one of a plurality of further "living hinges", 29ins, 29ins', 29ins" and 29ins''' connecting a corresponding one of a plurality of outer pivoting links, 30ins, 30ins', 30ins" and 30ins''' to an outer output structure. This output structure has a square opening, 31ins, in the center of a square plate thus forming a manipulable support 32ins.

Thus, inner pivoting link 20ins is connected by "living hinge" 25ins to outer pivoting link 30ins to be rotatable with respect thereto, and link 30ins in turn rotates about "living hinge" 29ins that connects that pivoting link to manipulable support 32ins. Similarly, pivoting link 20ins' is connected by "living hinge" 25ins' to pivoting link 30ins' which in turn rotates about "living hinge" 29ins' that connects that pivoting link to manipulable support 32ins. Also in this manner, pivoting link 20ins" is connected by "living hinge" 25ins" to pivoting link 30ins" which in turn rotates about "living hinge" 29ins" that connects that pivoting link to manipulable support 32ins. Lastly, pivoting link 20ins''' is connected by "living hinge" 25ins''' to pivoting link 30ins''' which in turn rotates about "living hinge" 29ins''' that connects that pivoting link to manipulable support 32ins.

As can be seen, pivoting links 20ins, 20ins', 20ins" and 20ins''' in the inner plurality thereof are each formed of a structural polymer (could alternatively be a metal) in a triangular shape when viewed from the "top" thereof with the triangle base occurring at the "living hinge" between the link and base 12ins commonly formed therewith. The link sides extend toward the opposite triangle apex that occurs where the corresponding one of linking "living hinges", 25ins, 25ins', 25ins" and 25ins''' is provided. Pivoting links 30ins, 30ins', 30ins" and 30ins'" in the outer plurality thereof are provided in the same manner with manipulable support 32ins.

The resulting structure in FIG. 3 for insertion joint 10' can be used to position manipulable support 32ins therein anywhere over a wide angular range by forcing inner pivoting links 20ins, 20ins', 20ins" and 20ins'" to selected rotational positions about the corresponding portion of base 12ins to which they are rotatably coupled by "living hinges" 22ins, 22ins', 22ins" and 22ins'", respectively (not all seen in FIG. 3). The performance of such a joint can be made quite repeatable if the structural members, especially the "living hinges" used therein, are carefully made with materials exhibiting the same properties from batch to batch as well as carefully maintaining essentially identical dimensions from batch to batch in each unit made such as by use of precise polymer molding or laser cutting techniques. In addition, insertion joint 10' can be made exceedingly small by using these methods.

Control joint 10" is formed typically of the same materials in the same manner and in the same configuration. However, this joint is not to have its output structure positioned by motion of the corresponding force imparting shafts, but rather the inverse is to occur. That is, the operator of inserter device arrangement 10 manipulates the position of the control joint outer structure, serving here as an input structure, to a desired angular orientation to change the positions of the force imparting shafts of this joint in translation. These translations are coupled to the force imparting shafts of insertion joint 10' to provide the desired angular orientation of its outer output structure as is described below.

Thus, control joint 10" is supported on a base, 12con, formed of a tubular portion extending from the left in FIG. 3 to the right with a passageway, 13con, through the center thereof opening circularly through a capping plate, 14con, (not seen in FIG. 3) formed as a center open square with its corners missing on corresponding diagonals thereacross, this plate being affixed to the right end of the tubular portion. Control joint 10" has a plurality of force imparting shafts, 15con, 16con, 17con and 18con, each extending from an unconnected end thereof on the right in the figure toward the left, and have in each of those unconnected ends a corresponding one of a plurality of notches, 19con, 19con', 19con" and 19con'". These shafts extend toward the left sufficiently to join a corresponding one of a plurality in inner pivoting links, 20con, 20con', 20con" and 20con'", through a corresponding one of a plurality of "living hinges", 21 con, 21 con', 21 con" and 21con'" (not all of these structures can be seen in this view). Force imparting shaft 16con is forced to move primarily in translation by rotating pivoting link 20con about a further "living hinge", 22con, connecting it to base 12con. In the same manner, force imparting shaft 17con is forced to move primarily in translation by rotating pivoting link 20con' about yet a further "living hinge", 22con', connecting it to base 12con. Again, force imparting shaft 18con is forced to move primarily in translation by rotating pivoting link 20con" about another "living hinge", 22con", connecting it to base 12con. Finally, force imparting shaft 15con is forced to move primarily in translation by rotating pivoting link 20con'" about yet another "living hinge", 22con'", that connects that pivoting link to base 12con.

Inner pivoting links 20con, 20con', 20con" and 20con'" are connected by a corresponding one of a plurality of linking "living hinges", 25con, 25con', 25con" and 25con'" to the outer portion of control joint 10" having a corresponding one of a plurality of further "living hinges", 29con, 29con', 29con" and 29con'" connecting a corresponding one of a plurality of outer pivoting links, 30con, 30con', 30con" and 30con'" to an outer input structure. This input structure has a square opening, 31con, in the center of a square plate thus forming a manipulable support 32con.

Thus, inner pivoting link 20con is connected by "living hinge" 25con to outer pivoting link 30con to be rotatable with respect thereto, and link 30con in turn rotates about "living hinge" 29con that connects that pivoting link to manipulable support 32con. Similarly, pivoting link 20con' is connected by "living hinge" 25con' to pivoting link 30con' which in turn rotates about "living hinge" 29con' that connects that pivoting link to manipulable support 32con. Also in this manner, pivoting link 20con" is connected by "living hinge" 25con" to pivoting link 30con" which in turn rotates about "living hinge" 29con" that connects that pivoting link to manipulable support 32con. Lastly, pivoting link 20con'" is connected by "living hinge" 25con'" to pivoting link 30con'" which in turn rotates about "living hinge" 29con'" that connects that pivoting link to manipulable support 32con.

As can be seen, pivoting links 20con, 20con', 20con" and 20con'" in the inner plurality thereof are each formed of a structural polymer (could alternatively be a metal) in a triangular shape when viewed from the "top" thereof with the triangle base occurring at the "living hinge" between the link and base 12con commonly formed therewith. The link sides extend toward the opposite triangle apex that occurs where the corresponding one of linking "living hinges", 25con, 25con', 25con" and 25con'" is provided. Pivoting links 30con, 30con', 30con" and 30con'" in the outer plurality thereof are provided in the same manner with manipulable support 32con.

A turning knob, 33, having a shape something like a hemisphere mounted on a tubular pedestal has the passageway within that tubular portion extend also as a passageway opening through the hemisphere so that this opening is aligned with the tubular passageway. The tubular portion of turning knob 33 is positioned in opening 31 con of manipulable support 32con and is ultrasonically welded to this support at that position when assembled or otherwise affixed therein. A fairly rigid plastic material can be used for this knob so that it holds its shape despite the operator squeezing it and so that it can be rotated to rotate control joint 10" as will be described below.

As indicated above, an operator of inserter device arrangement 10 can manipulate the angular position of manipulable support 32con of control joint 10" to a desired angular orientation to thereby change, through the resulting angular positional change of outer pivoting links 30con, 30con', 30con" and 30con'", the relative rotational positions of inner pivoting links 20con, 20con', 20con" and 20con'" with respect to one another about "living hinges" 21con, 21con', 21con" and 21 con'". This result changes the relative positions of force imparting shafts 15con, 16con, 17con and 18con primarily in translation with respect too one another. These different translations are coupled by a corresponding one of a plurality of coupling shafts, 35, 36, 37 and 38, shown in FIG. 3, to force imparting shafts 15ins, 16ins, 17ins and 18ins of insertion joint 10', respectively, to thereby change the relative rotational positions of inner pivoting links 20ins, 20ins', 20ins" and 20ins'" with respect to one another about "living hinges" 21 ins, 21 ins', 21 ins" and 21ins'". This forces changes in the angular positions of outer pivoting links 30ins, 30ins', 30ins" and 30ins'" to thereby provide the desired angular orientation of manipulable support 32ins.

Thus, coupling shaft 35 has a notch at its left end that is complementally fitted into notch 19con'" of force imparting shaft 15con and typically ultrasonically welded thereto (although the alternative use of an adhesive or the performing of a fusing might be done for such joining instead) to be permanently joined together when assembled as will be shown in subsequent figures. Coupling shaft 35 also has a notch at its right end that is complementally fitted into notch 19ins''' of force imparting shaft 15ins and typically ultrasonically welded thereto when assembled again as will be shown in subsequent figures. Similarly, coupling shaft 36 has a notch at its left end that is complementally fitted into notch 19con of force imparting shaft 16con and typically ultrasonically welded thereto when assembled, and further has a notch at its right end that is complementally fitted into notch 19ins of force imparting shaft 16ins and typically ultrasonically welded thereto when assembled. Again, coupling shaft 37 has a notch at its left end that is complementally fitted into notch 19con' of force imparting shaft 17con and typically ultrasonically welded thereto when assembled, and further has a notch at its right end that is complementally fitted into notch 19ins' of force imparting shaft 17ins and typically ultrasonically welded thereto when assembled. Finally, coupling shaft 38 has a notch at its left end that is complementally fitted into notch 19con'' of force imparting shaft 18con and typically ultrasonically welded thereto when assembled, and further has a notch at its right end that is complementally fitted into notch 19ins'' of force imparting shaft 18ins and typically ultrasonically welded thereto when assembled.

Coupling shafts 35, 36, 37 and 38 are formed of "engineered plastics" such as the high modulus class of plastics known as ABS plastics for greater stiffness in being better able thereby to transmit translational motion therethrough. Although these coupling shafts joining respective ones of force imparting shafts 15con, 16con, 17con and 18con to force imparting shafts 15ins, 16ins, 17ins and 18ins are sufficient to allow an operator to use control joint 10'' to set the angular orientation of manipulable support 32ins of insertion joint 10', they are insufficient of themselves to allow the operator to change the degree of elongation of either of these joints.

For this purpose, there is further shown in FIG. 3 two cylindrical shell separators, 39 and 40, each having a shell wall with a cross sectional configuration of a cruciform shaped shell with four cruciform shell arms extending outward from the symmetrical axis at the shell center, but with the projected inward crossing point of these arms at the shell interior being eliminated. This elimination is because of an intervening interrupted circular shell wall passageway about the symmetry axis leaving the outer remainders of the cruciform shell arms being symmetrically formed about, and merged into, this interrupted circular shell wall passageway as the interruptions thereto, the passageway being centered about the point of symmetry on the symmetry axis at which the cruciform arms would otherwise have met. As a result, there are symmetrically located recesses in the outer surfaces of these separator shell walls each formed by the space between adjacent ones of the four symmetrically positioned, cruciform shaped cross section shell arms also formed by these walls.

In addition, there is also shown a slideway, 41, again with a cross sectional configuration of a cruciform shape having its interior at, and near, the central axis of symmetry eliminated by an intervening circular shell wall passageway, though uninterrupted here, so that the outer remainders of the solid cruciform arms are symmetrically formed about and merged into this shell wall circular passageway again centered about the point of symmetry on the symmetry axis at which the cruciform arms would otherwise have met. Here too, there are symmetrically located recesses in the outer surfaces of the structure formed by the spaces between the four solid cruciform shaped arms attached to, and positioned symmetrically about, the periphery of the circular passageway shell wall, these recesses each being between adjacent ones of these four symmetrically positioned, cruciform shaped cross section arms. The extents of the cross section shape of slideway 41 in various directions therethrough are a bit less than the extents at similar locations in similar directions through the cross section shapes of separators 39 and 40 (which substantially match one another) so that slideway 41 can be inserted into the interior of either of separators 39 and 40.

Slideway 41 is partially positioned within the interior of the shell walls of separator 39 at one end thereof and affixed there when assembled by ultrasonic welding or other suitable means of providing such fixation with the solid cruciform shaped arms thereof in the interiors of corresponding ones of the separator cruciform shell arms so that the recesses in the separator and the slideway are aligned. At the other end of separator 39, the tubular portion of base 12con of control joint 10'' is substantially fully positioned within the interior of the circular passageway of the shell walls of separator 39 and again affixed there when assembled by ultrasonic welding or other suitable means of providing such affixation. Similarly, at one end of separator 40, the tubular portion of base 12ins of insertion joint 10' is substantially fully positioned within the interior of the circular passageway of the shell walls of separator 40 and again affixed there when assembled by ultrasonic welding or other suitable means of providing such affixation. Slideway 41 is also partially positioned within the interior of the shell walls of separator 40 at the other end thereof when assembled though not affixed there so that it is free to slide back and forth with respect to separator 40. Again, the solid cruciform shaped arms of the slideway are in the interiors of corresponding ones of the separator cruciform shell arms so that the recesses in both separators and the slideway are aligned.

Each of the shaft assemblies of one of coupling shafts 35, 36, 37 and 38, along with portions of the corresponding one of force imparting shafts 15con, 16con, 17con and 18con and of force imparting shafts 15ins, 16ins, 17ins and 18ins affixed thereto when assembled, is positioned in a corresponding one of the aligned recesses in separators 39 and 40 that are joined in a common recess by the corresponding recess in slideway 41. Such an assembled result is shown in the side view presented, to some extent schematically, in FIG. 4 and in the two cross section views thereof shown in FIGS. 5 and 6 where the dashed line circles represent an outer tube in inserter arrangement 10 that is shown in FIGS. 1 and 2 but not in FIGS. 3 and 4 for purposes of clarity. Except in one exemplar section of separator 40, the two symmetrically positioned, cruciform shaped cross section shell arms thereof seen in FIG. 4 are represented by alternating paired dots and dashed lines position approximately at the outer ends thereof.

However, although slideway 41 is also partially positioned within the interior of the shell walls of separator 40 at the other end thereof when assembled, it is not affixed there as indicated above but, instead, separator 40 is free to slide back and forth some distance along slideway 41 as determined by the operator of inserter device arrangement 10 using an activator arrangement to be described in the following. Thus, sliding separator 40, in being slid toward separator 39 on slideway 41, pulls base 12ins of insertion joint 10' toward control joint 10'' which in turn pulls on inner pivoting links 20ins''', 20ins', 20ins'' and 20ins of insertion joint 10' that then push on force imparting shafts 15ins, 16ins, 17ins and 18ins, respectively, which in turn push on coupling shafts 35, 36, 37 and 38, respectively. Coupling shafts 35, 36, 37 and 38 in turn push on force imparting shafts 15con, 16con, 17con and 18con, respectively, which in turn push on inner pivoting links 20con, 20con', 20con" and 20con'", respectively, causing them to pull on base 12con.

At the same time, the pulling by base 12ins on inner pivoting links 20ins'", 20ins', 20ins" and 20ins causes them to rotate toward the center about "living hinges" 21ins, 21ins', 21ins" and 21ins'". This results in inner pivoting links 20ins, 20ins', 20ins" and 20ins'" and outer pivoting links 30ins, 30ins', 30ins" and 30ins'" both rotating about linking "living hinges" 25ins, 25ins', 25ins" and 25ins'" so that outer pivoting links 30ins, 30ins', 30ins" and 30ins'" also rotate toward the center about "living hinges" 29ins, 29ins', 29ins" and 29ins'". As a result, insertion joint 10' tends to become elongated.

Since base 12con is affixed to separator 39 it cannot move to thereby result in inner pivoting links 20con, 20con', 20con" and 20con'", in pulling on that base, also rotating toward the center about "living hinges" 21con, 21con', 21con" and 21con'". This results in inner pivoting links 20con, 20con', 20con" and 20con'" and outer pivoting links 30con, 30con', 30con" and 30con'" both rotating about linking "living hinges" 25con, 25con', 25con" and 25con'" so that outer pivoting links 30con, 30con', 30con" and 30con'" also rotate toward the center about "living hinges" 29con, 29con', 29con" and 29con'". As a result, control joint 10" is elongated, and to the maximum extent possible if separator 40 is moved as far as possible toward separator 39. Once control joint 10" approaches the maximum possible elongation thereof, the rigidity of coupling shafts 35, 36, 37 and 38 will also cause insertion joint 10' to approach its maximum possible elongation thereby giving the result for these joints depicted in FIG. 1 which, as stated above, is a condition in which the angular orientation of manipulable support 32ins cannot be changed as desired by the operator since the inner operating links of both joints are forced toward the center as far as possible.

In contrast, sliding separator 40, in being slid away from separator 39 on slideway 41, pushes base 12ins of insertion joint 10' away from control joint 10" which in turn pushes on inner pivoting links 20ins'", 20ins', 20ins" and 20ins of insertion joint 10' that then pull on force imparting shafts 15ins, 16ins, 17ins and 18ins, respectively, which in turn pull on coupling shafts 35, 36, 37 and 38, respectively. Coupling shafts 35, 36, 37 and 38 in turn pull on force imparting shafts 15con, 16con, 17con and 18con, respectively, which in turn pull on inner pivoting links 20con, 20con', 20con" and 20con'", respectively, causing them to push on base 12con.

At the same time, the pushing by base 12ins on inner pivoting links 20ins'", 20ins', 20ins" and 20ins causes them to rotate away from the center about "living hinges" 21ins, 21ins', 21ins" and 21ins'". This results in inner pivoting links 20ins, 20ins', 20ins" and 20ins'" and outer pivoting links 30ins, 30ins', 30ins" and 30ins'" both rotating about linking "living hinges" 25ins, 25ins', 25ins" and 25ins'" so that outer pivoting links 30ins, 30ins', 30ins" and 30ins'" also rotate away from the center about "living hinges" 29ins, 29ins', 29ins" and 29ins'". As a result, insertion joint 10' tends to have its length reduced but its diameter in planes perpendicular there to increased.

Since base 12con is affixed to separator 39 it cannot move thereby resulting in inner pivoting links 20con, 20con', 20con" and 20con'", in pushing on that base, also rotating away from the center about "living hinges" 21con, 21con', 21con" and 21con'". This results in inner pivoting links 20con, 20con', 20con" and 20con'" and outer pivoting links 30con, 30con', 30con" and 30con'" both rotating about linking "living hinges" 25con, 25con', 25con" and 25con'" so that outer pivoting links 30con, 30con', 30con" and 30con'" also rotate away from the center about "living hinges" 29con, 29con', 29con" and 29con'". As a result, control joint 10" has its length reduced but its diameter in planes perpendicular there to increased, and to the maximum extent possible if separator 40 is moved as far as possible away from separator 39.

Once control joint 10" approaches the maximum possible elongation thereof, the rigidity of coupling shafts 35, 36, 37 and 38 will also cause insertion joint 10' to approach its minimum possible elongation thereby giving the result for these joints depicted in FIG. 2 which, as stated above, is a condition in which the angular orientation of manipulable support 32ins can be changed as desired by the operator since the inner operating links of both joints are free to have their relative angular positions changed with respect to one another through the forces resulting from the angular operator changing the angular orientation of manipulable support 32con as is shown in the one angular positioning example depicted in FIG. 7. Note that changing the angular orientation of manipulable support 32con to a different angular position results in the changing the angular orientation of manipulable support 32ins to a complementary angular position, i.e. to the negative angular position with respect to the angular position of manipulable support 32con.

Figure 8:
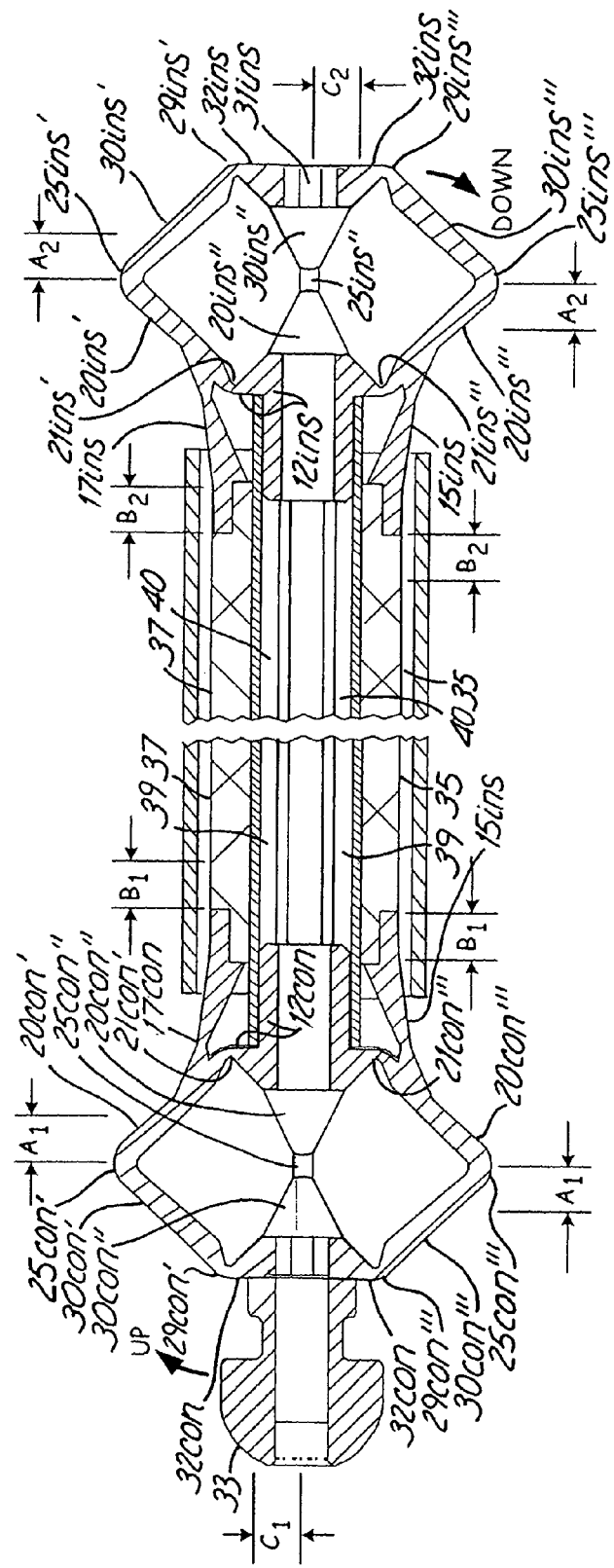
FIG. 8 is a partial side view of the assembly shown in FIG. 4.

This relative angular position change relationship between manipulable support 32con and manipulable support 32ins can be seen more clearly in the enlarged, although only partly broken out, version of the side view of the structure depicted in FIG. 4 that is presented in FIG. 8. There, although turning knob 33 can be moved to any angular position with respect to the axis of symmetry extending along the length of its passageway, the representations in FIG. 8 are some resulting associated approximate translations for various potions of the structure shown there due to the arbitrary choice of swinging the left end of knob 33 directly upward, as indicated by the arrow and the word "up" shown there. Each translation result depicted is represented by pairs of spaced apart vertical lines of which one is over the initial position of the adjacent structure portion, and that together are indicated to be translation distances through the providing of opposed arrows on the outsides of each such line pair along with a distance designation for the approximate translation distance represented being provided therebetween.

Thus, turning knob 33, if manually rotated directly upward in FIG. 8 by an angle sufficient to cause the axis of symmetry extending along the length of its passageway to move from a horizontal position, indicated by the line below the translation distance $C_1$, to an angular position such that this axis at the left end of knob 33 has translated vertically upward a distance of $C_1$, there will be corresponding position changes for the remainder of the structure shown in that figure. The translations occurring in these position changes for some of the structure portions are indicated by the pairs of spaced apart vertical lines mentioned above. So, "living hinge" 25con' in control joint 10" will change its angular position sufficiently to translate in doing so a distance from left to right of $A_1$, while "living hinge" 25con'" will change its angular position sufficiently to translate in doing so a distance from right to left of $A_1$. This will push force imparting shaft to the right in the figure a distance of $A_1$, and will pull force imparting shaft 15con to the left also a distance of $A_1$.

These movements of force imparting shafts 15con and will push the left end of coupling shaft 37 to the right in the figure a distance of $B_1$, and will pull the left end of coupling shaft 35 to the left also a distance of $B_1$. As a result, the right end of coupling shaft 37 will be moved to the right in the figure a distance of $B_2$, and will pull the right end of coupling shaft 35 to the left also a distance of $B_2$ where distance $B_2$ will be very nearly equal to distance $B_1$. This, in turn, will force "living hinge" 25ins' in insertion joint 10' to change its angular position sufficiently to translate in doing so a distance from left to right of $A_2$, while "living hinge" 25ins''' will change its angular position sufficiently to translate in doing so a distance from right to left of $A_2$. The angular position of manipulable support 32ins will thereby be changed such that the axis of symmetry of opening 31ins therein will rotate downward form a horizontal position to an angular position sufficient for that axis at the right of that opening to translate vertically downward a distance of $C_2$ which the negative of the angular change of turning knob 33 in accord with the statement made above.

Thus, turning knob 33, affixed to control joint 10", can be used in the structure shown in FIGS. 4, 5, 6 and 8 to angularly position the direction pointed toward by the axis of symmetry of opening 31ins in manipulable support 32ins of insertion joint 10'. This structure must, however, be further operated and controlled so as to be able to shorten and elongate joints 10' and 10" to accommodate the insertion of insertion joint 10' into the entity into which some selected item (here, by example, electrical interconnection lead $10^{iv}$) is to be inserted, and must also be protected from interference from such an entity during such insertions. The remainder of inserter arrangement 10 with this structure positioned within allows accomplishing these goals while also allowing turning knob 33 to be used to rotate both insertion joint 10' and the selected item for insertion.

Figure 9:
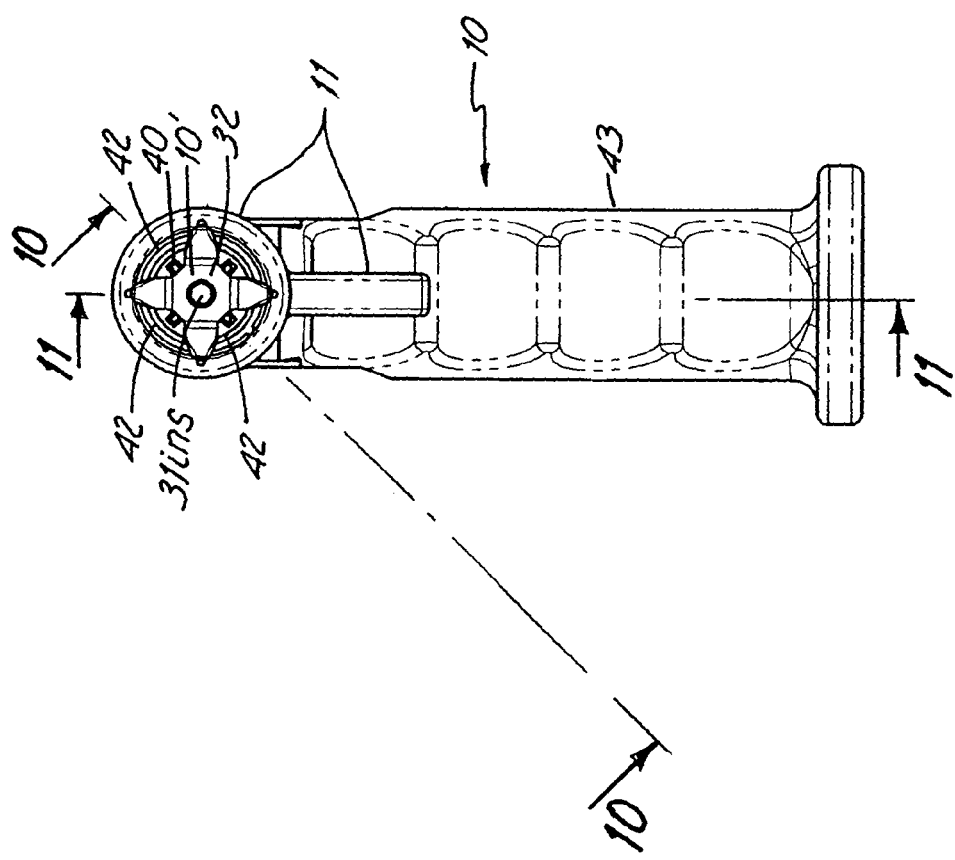
FIG. 9 is a front view of the embodiment shown in FIG. 1, FIGS. 10 and 11 are cross section views of a portion of the embodiment shown in FIG. 9.

The configuration of this structure in inserter arrangement 10 is seen in the cross section views indicated on the front view of inserter arrangement 10 shown in FIG. 9. As can be seen, the cross section views in FIGS. 10 and 11, which are more or less side views, are each presented at a corresponding viewing angle different from that of the other with respect to the axis of symmetry of opening 31ins in manipulable support 32ins of insertion joint 10'.

As can be seen in FIG. 9, a barrel, 42, in substantially the form of a circular cross section cylindrical shell is the main addition to the arrangement shown in FIG. 7 to complete inserter device arrangement 10, that barrel not being shown in FIG. 7 for the purpose of clarifying the position of the primary portion of the operating structure previously shown in FIGS. 3, 4, 5, 6 and 8 with respect to much of the rest of that device. Thus, as seen in FIG. 9, the structure shown in FIGS. 3, 4, 5, 6 and 8 is fitted within the interior passageway of barrel 42. The cross-section views provided in FIGS. 10 and 11, as marked in FIG. 9, show in more detail the position of the portion of the primary operating structure shown in FIGS. 3, 4, 5, 6 and 8 which remains after the sectioning thereof in FIGS. 10 and 11 with respect to barrel 42 of inserter device arrangement 10.

Figure 10:
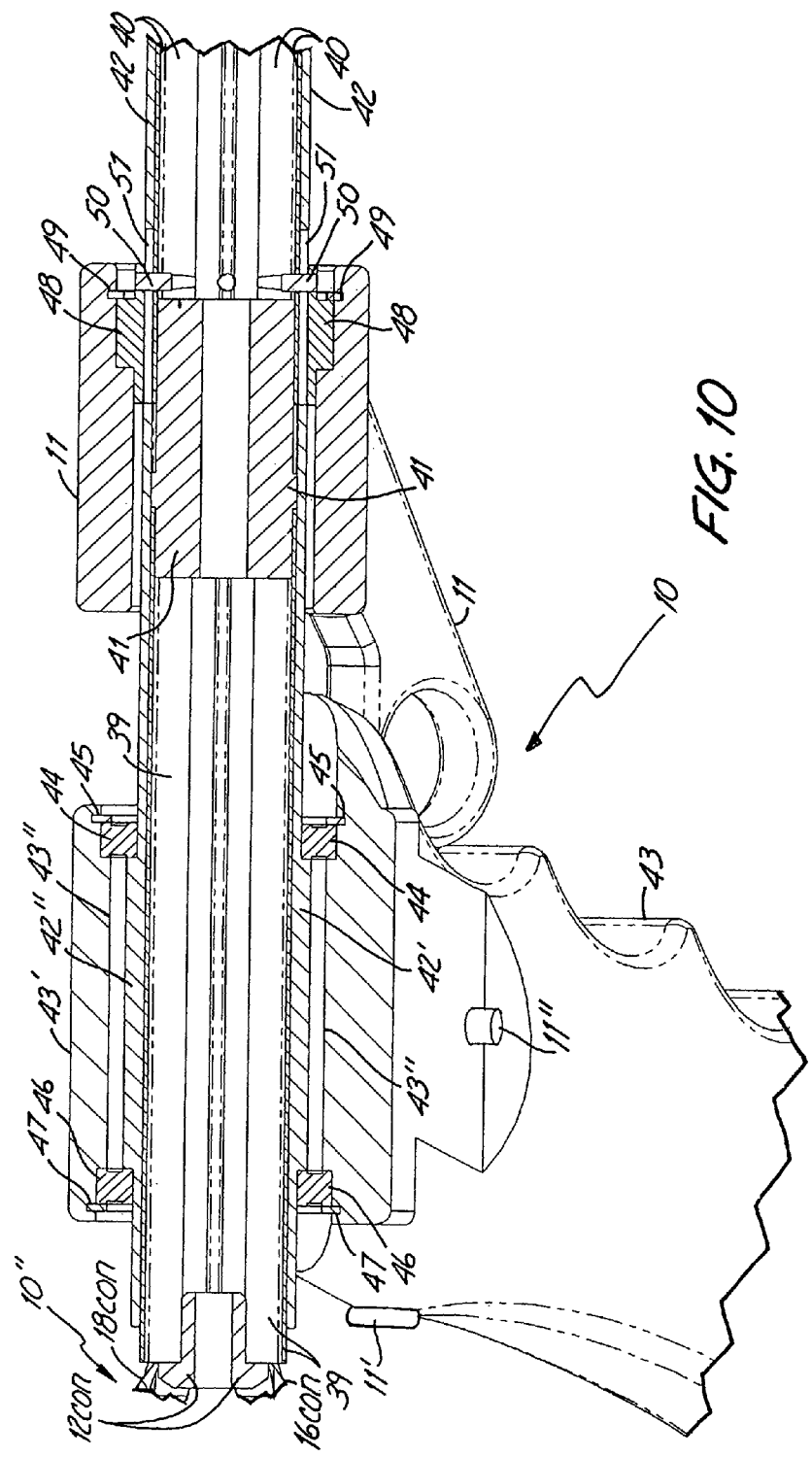
Figure 11:
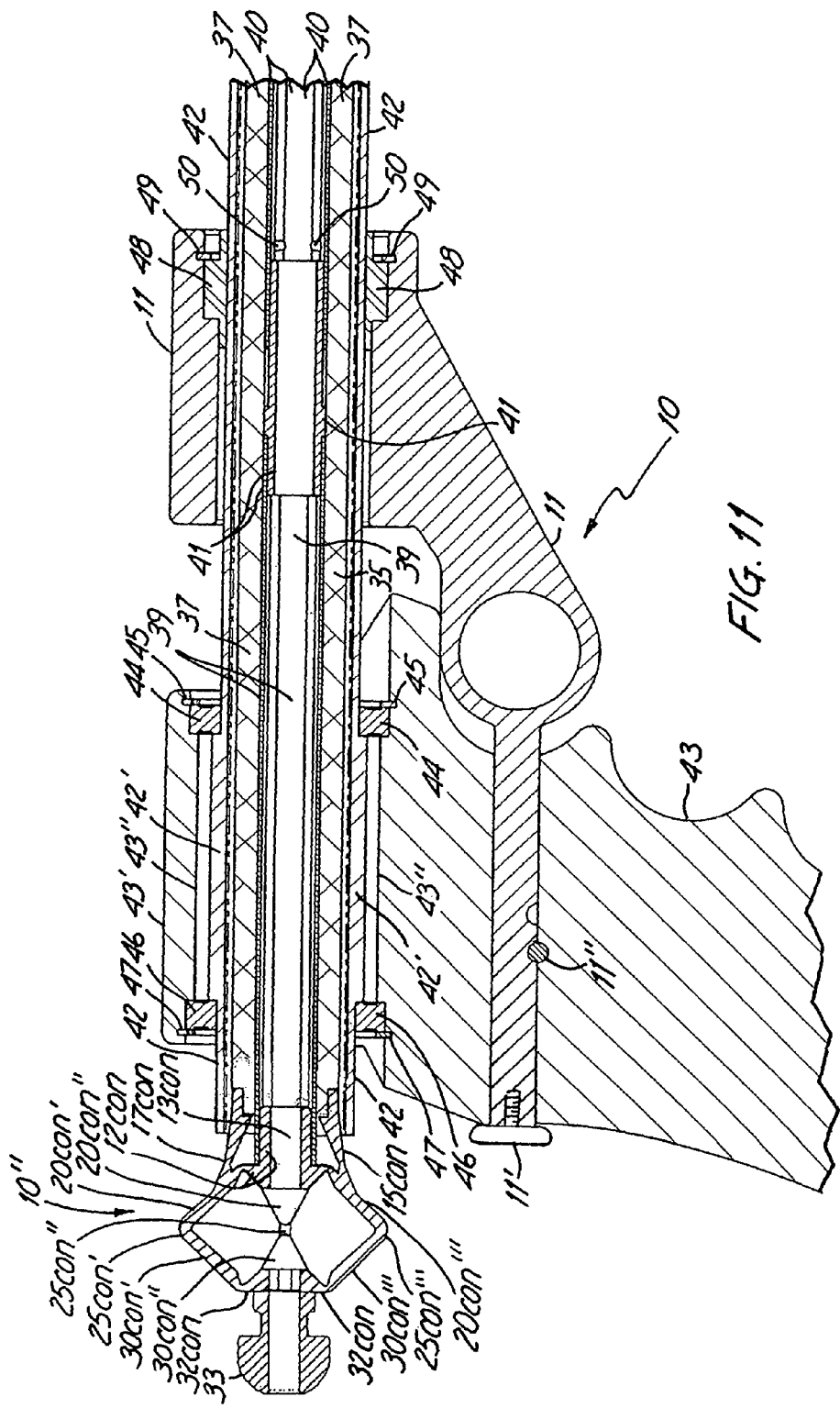

Barrel 42 has a greater exterior diameter portion, or thickened wall portion, 42', about the periphery thereof near its left end in FIGS. 10 and 11 to thereby form two shoulders in the outer surface of barrel 42 encircling thereabout on either end of this thickened wall portion where the extending outward of the barrel wall in greater diameter from the rest of the barrel outer surface begins. Thickened wall portion 42' near the lower side thereof is positioned on a hand grip, 43, within a bearing housing, 43', formed as an extension of hand grip 43 in extending from either side of that hand grip to be about thickened wall portion 42' of barrel 42 to form a bore therethrough accommodating that thickened wall portion therein. Bearing housing 43' has a smaller interior diameter portion with respect to the remainder of the interior bore surface to thereby form a thickened interior wall portion, 43", extending about the interior bore thereof, and so about thickened wall portion 42' of barrel 42, including as a part thereof a raised portion of hand grip 43 below barrel 42 in FIGS. 10 and 11. Thickened interior wall portion 43" thus provides a shoulder at each end thereof encircling about the interior bore of bearing housing 43' and the raised portion 43" of hand grip 43 where the interior housing wall extending inward from the remainder of the bore surface begins.

A bearing assembly, 44, is positioned against both the right side shoulder in FIGS. 10 and 11 provided by thickened wall portion 42' of barrel 42 and the right side shoulder of thickened interior wall portion 43" of bearing housing 43', including the raised portion thereof in hand grip 43, and retained there by snap ring, 45. The outer race of ball bearing assembly 44 is affixed to thickened interior wall portion 43" of bearing housing 43' including the raised portion of hand grip 43 therein, and the inner race of ball bearing assembly 44 is affixed to barrel 42 so that this race and barrel 42 can rotate with respect to bearing housing 43'.

Similarly, a bearing assembly, 46, is positioned against both the left side shoulder provided by thickened wall portion 42' of barrel 42 and the left side shoulder of thickened interior wall portion 43" of bearing housing 43', including the raised portion thereof in hand grip 43, and retained there by snap ring, 47. The outer race of ball bearing assembly 46 is affixed to thickened interior wall portion 43" of bearing housing 43' including the raised portion of hand grip 43 therein, and the inner race of ball bearing assembly 46 is affixed to barrel 42 so that this race and barrel 42 can rotate with respect to bearing housing 43'.

This arrangement allows barrel 42 and the primary operating structure of FIGS. 3, 4, 5, 6 and 8 positioned within that barrel to be rotated with respect to hand grip 43 and bearing housing 43' by rotating turning knob 33 about the axis of symmetry of the passageway therethrough. Alternative to the use of ball bearing assemblies 44 and 46, a bushing could be provided instead between thickened wall portion 42' of barrel 42 and thickened interior wall portion 43" of bearing housing 43' including the raised portion of hand grip 43 therein.

Such rotating of barrel 42 with the primary operating structure of FIGS. 3, 4, 5, 6 and 8 mounted therein requires that both also be rotatable within slide barrel 11 provided thereabout as shown in FIGS. 9, 10 and 11. Thus, the interior bore of slide barrel 11 has an enlarged interior diameter at the right end thereof in FIGS. 10 and 11 to form an interior shoulder circumscribe by that bore where the interior bore surface begins to extend outward. A rotatable collar, 48, is held by a snap ring, 49, against this slide barrel bore shoulder. Rotatable collar 48 is free to rotate between this slide barrel bore shoulder in slide barrel 11 and snap ring 49 as shown in these figures, but could augmented in doing so by the use of bearing assemblies or bushings if sufficiently desirable to thereby reduce friction.

A set of four pins, 50, are each anchored at one end thereof in rotatable collar 48 from where the remainder of each extends through a corresponding one of slots, 51, in barrel 42 to then further extend through a corresponding circular opening in the adjacent outermost portion of a corresponding one of the cruciform shell arms of shell separator 40. These pins allow slide barrel 11, in being moved back and forth along barrel 42 by an operator of inserter device arrangement 10, to thereby move separator shell 40 back and forth along slideway 41. As a result, the operator of inserter device arrangement 10 is thereby permitted to change the degree of elongation of insertion joint 10' as described above. Yet the anchoring of pins 50 in rotatable collar 48 allows the rotating of barrel 42 and the structure of FIGS. 3, 4, 5, 6 and 8 positioned therein in accord with any rotating of turning knob 33 in having rotatable collar 48 rotate therewith inside of nonrotating slide barrel 11.

Figure 12:
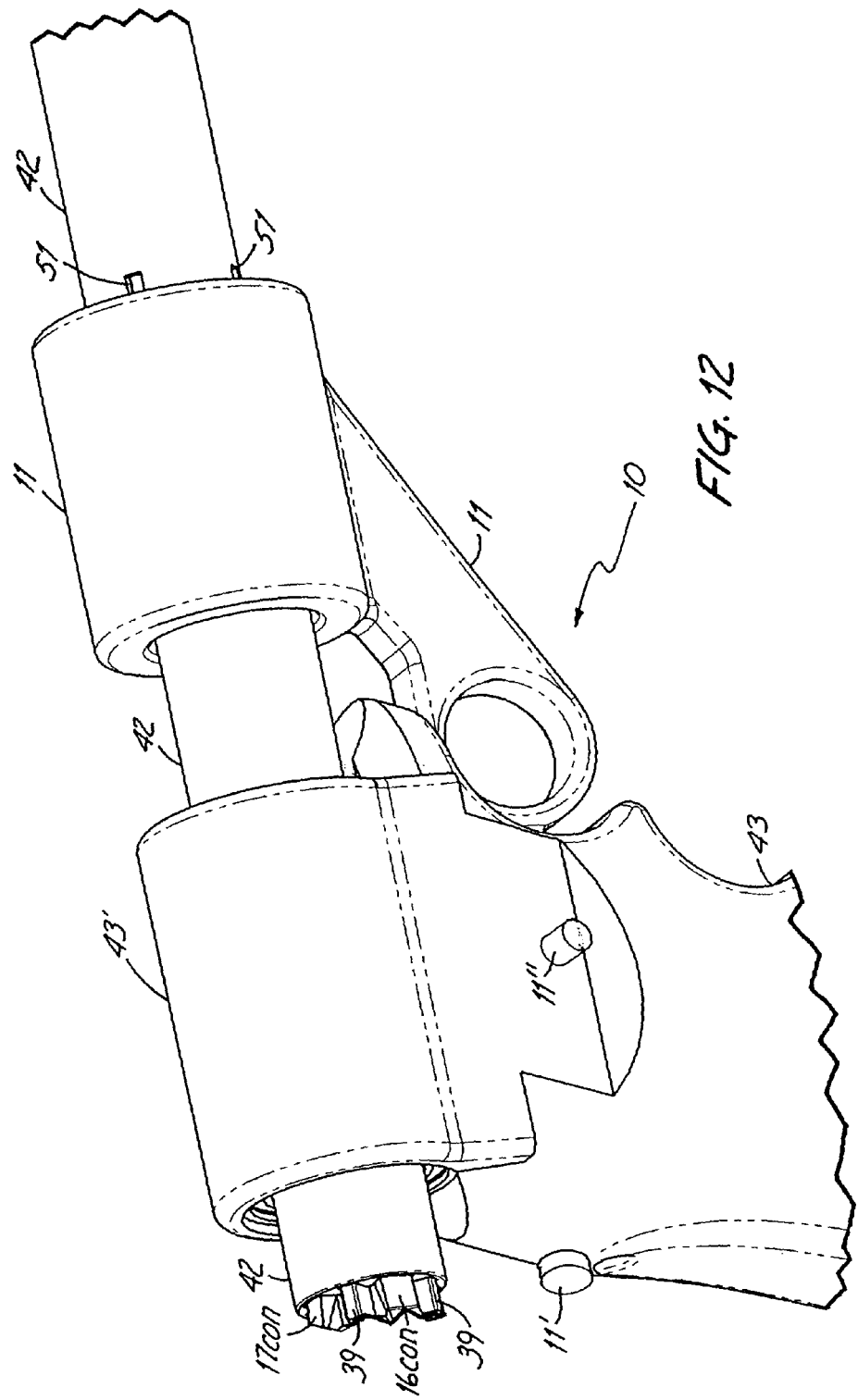
FIG. 12 is a perspective view of a portion of the embodiment shown in FIG. 2.
Figure 13:
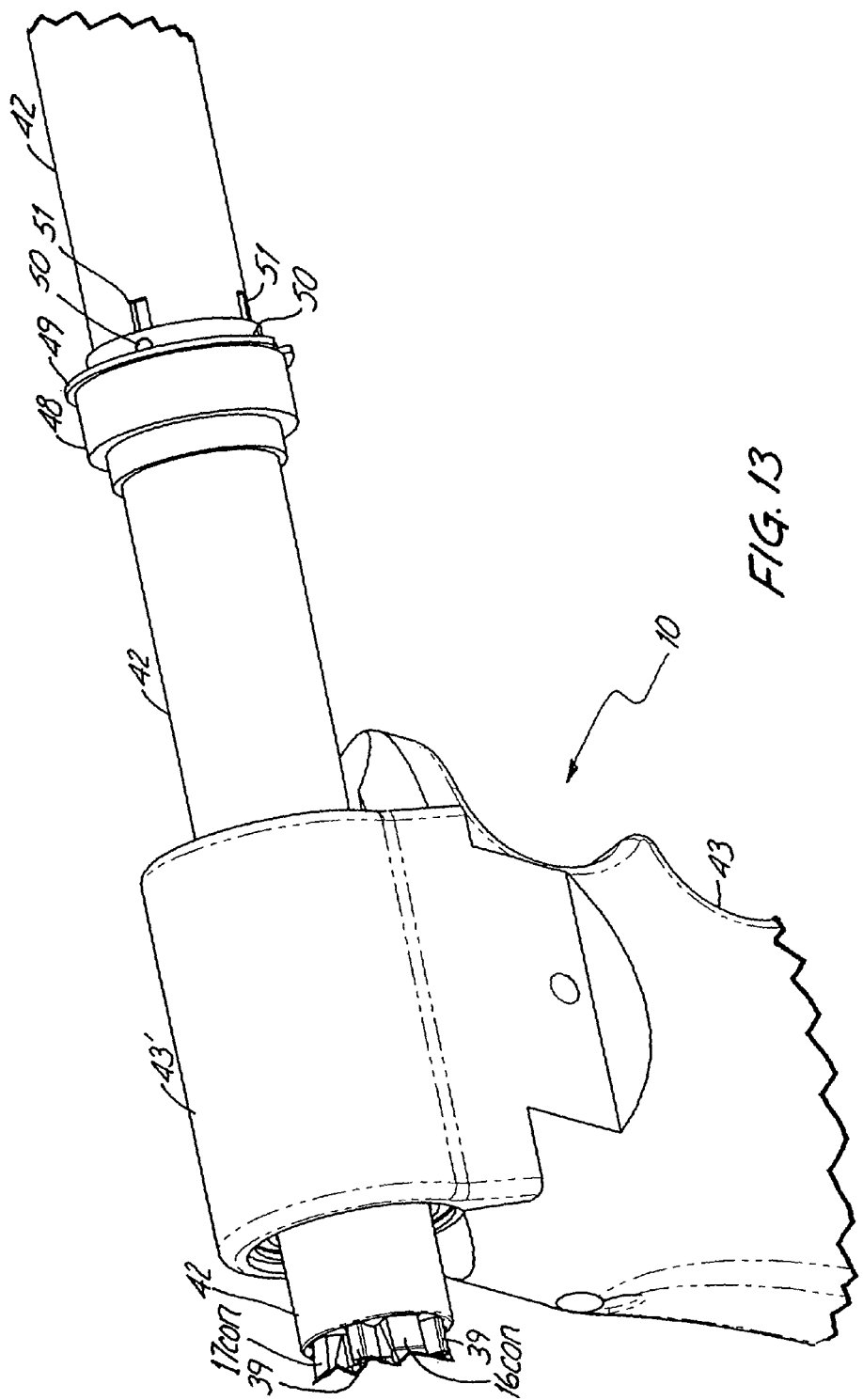
FIG. 13 is a perspective view of a partially disassembled portion of the embodiment shown in FIG. 12.

The relationship between slide barrel 11, rotatable collar 48, pins 50 in extending through slots 51 of barrel 42, to enter the cruciform arms of separator 40 can perhaps be better appreciated through the partial disassembly sequence of inserter device arrangement 10 presented in FIGS. 12, 13 and 14. This sequence with inserter device arrangement 10 fully assembled starts in FIG. 12 which is a fragmented view showing a portion of inserter device arrangement 10 taken from FIG. 1, and presents there a portion of hand grip 43, all of bearing housing 43' and slide barrel 11 along with push bar 11' and lock bar 11", and a portion of barrel 42 that are together found in a central portion of inserter device arrangement 10 as shown in FIG. 1.

FIG. 13 shows the inserter assembly again but with slide barrel 11, push bar 11' and lock bar 11" being removed to expose a greater portion of barrel 42 and to expose much of the outer surfaces of rotatable collar 48 and snap ring 49. In addition, the ends of pins 50 as anchored in rotatable collar 48 can be seen along with a greater portion of slots 51. FIG. 14 shows the remainder of inserter arrangement 10 following the removal of rotatable collar 48 and snap ring 49 to show all of two of slots 51 and portions of three of pins 50 in those slots and one further such slot unseen in this view.

All of the structures shown in FIG. 13 along barrel 42 can be rotated by turning knob 33, not shown, within bearing housing 43'. The back and forth movement of rotatable collar 48 through moving slide barrel 11 in which collar 48 is held by snap ring 49 causes pins 50 to slide back and forth in the slots of barrel 42 and correspondingly move separator 40 back and forth within barrel 42 to change the degree of elongation of insertion joint 10' and of control joint 10".

FIG. 15 shows a cross-section view of FIG. 9 somewhat similar to that shown in FIG. 11 but providing more sectioning and also showing the extreme right end of barrel 42 and insertion joint 10' in this view. This view is primarily to show the arrangement for allowing slide barrel 11 to be locked in an extreme position to the right, as shown in FIG. 15, by lock bar 11" so as to shorten the longitudinal extents of insertion joint 10' and control joint 10". In the alternative, slide barrel 11 is locked to the extreme left position by lock bar 11", this situation not being shown in FIG. 15, to cause insertion joint 10' and control joint 10" to be in their relatively elongated longitudinal extents.

Lock bar 11" locks slide barrel 11 in either of these two extreme positions thereof through having a portion of that bar, exhibiting its full diameter, positioned in one of two alternative semicircular profile cross-section notches, 52, provided in the oblong extension of slide barrel 11 that provides push bar 11' which extends through hand grip 43 from front to back thereof. As can be seen in the partial cross section view in FIG. 15A taken from FIG. 15 as marked there, lock bar 11" can be pushed to the right in hand grip 43 to have a portion thereof exhibiting its full diameter positioned in either one of notches 52 in push bar 11'. Alternatively, lock bar 11" can be pushed to toward the left to have a semicircular profile cross-section notch, 53, in that lock bar aligned with push bar 11' so that push bar 11' can be moved back and forth between its extreme right and extreme left positions in FIG. 15. Once slide barrel 11 and push bar 11' are positioned in the one of the extreme positions available therefor selected by the operator of inserter device arrangement 10, lock bar 11" can be pushed by the operator to the right in hand grip 43 to have the portion thereof exhibiting its full diameter positioned in the corresponding one of notches 52 in push bar 11' that is then correspondingly located adjacent to lock bar 11".

Returning to FIG. 3, electrical interconnection lead $10^{iv}$ is shown having a long electrical conductor, 55, which, for the operation of inserting this lead in a biological object, is positioned in inserter device arrangement 10 by the operator thereof to extend through openings 31ins and 13ins of insertion joint 10', and then continue through the central passageways of separator 40, slideway 41, and separator 39. Electrical conductor 55 then passes through openings 13con and 31con of control joint 10" to emerge from the passageway through turning knob 33 as is seen in FIGS. 1 and 2. Electrical conductor 55 emerges from a square nut portion, 56, of the polymer molded interconnection lead base, 57, that is completed by a disk, 58, integrally molded with nut 56 on one major surface thereof. Disk 58 has a helical shaped electrical conductor, 59, emerging from its opposite major surface that is mounted therein such that this helical conductor is an electrical contact with long conductor 55. Helical conductor 59 has a sharpened opposite end from where it emerges so that rotating base 57 results in helical conductor 59 also being rotated.

Hence, if helical conductor 59 has been pressed against biological tissue by inserter arrangement 10 for such rotating, helical conductor will be "screwed" into that biological tissue against which it has been positioned to thereby enter and engage with that tissue much as a corkscrew does in a cork of a wine bottle in securely engaging that cork preliminary to its removal from the bottle. The positioning of square nut 56 in squared out opening 31ins of insertion joint 10' allows such rotating of base 57 to occur as a result of the corresponding rotating of turning knob 33 which in turn causes rotation of the entire assembly involving that knob, control joint 10", separator 39, slideway 41, separator 40 and insertion joint 10' in which interconnection lead $10^{iv}$ is positioned as described in the preceding.

Prior to inserting and screwing interconnection lead $10^{iv}$ into selected biological tissue, there is sometimes a need to cut away an outer layer of that tissue to allow such an insertion of lead $10^{iv}$ to be more easily done, or more securely mounted, or both. Thus, a vacuum based tissue cutter, 60, is shown above interconnection lead $10^{iv}$ in FIG. 3, and this cutter has a small diameter, small bore vacuum tube, 61, which is positioned in the same path through inserter arrangement 10 as was electrical conductor 55 (in the description thereof just given above) in preparation for performing the cutting operation. Again, a square nut, 62, is part of a molded polymer base, 63, with tube 61 entering that nut. Base 63 has a cutting knife, 64, mounted therein on the side of base 63 opposite that in which vacuum tube 61 enters base 63.

These arrangements are better seen in the side view of FIG. 16 in which base 63 is presented in cross section to better show the internal construction thereof. Vacuum tube 61 passes through base 63 from molded nut 62 side thereof to emerge on the opposite side from which knife 64 extends. Vacuum tube 61 on this latter side is mounted to the center rear of a hemispherical soft silicone rubber cup, 65, so that the bore of the tube opens in the interior of the cup.

Vacuum cutter 60 is positioned in inserter device arrangement 10 prior to mounting interconnection lead $10^{iv}$ therein for the purpose, indicated above, of cutting away biological tissue in preparation for the subsequent substitution of interconnection lead $10^{iv}$ for vacuum cutter 60 in inserter arrangement 10, or another such inserter, to then complete the insertion and attachment of that lead in the biological tissue. With vacuum cutter 60 in inserter device arrangement 10 and positioned by the operator against the biological object of interest, a suitable vacuum is established at the opposite end of tube 61 which in turn causes that biological material against which cup 65 has been positioned to somewhat conform to the interior of the cup and so be pulled somewhat away from the underlying tissue. In that circumstance, with molded nut 62 positioned in square opening 31ins of insertion joint 10', the rotating of turning knob 33 causes base 63 to rotate about vacuum hose 61 so that the end of knife 64, which has penetrated the outer biological tissue layer due to its being pulled there against by the vacuum established in cup 65, cuts away a circular portion of that layer with a diameter just greater than that of cup 65.

Removal of inserter device arrangement 10 while maintaining the vacuum in vacuum tube 61 allows this biological object outer layer portion that has been cut away to be removed contemporarily with that removal of inserter arrangement 10. Electrical interconnection 10$^{iv}$ can then be substituted for vacuum cutter 60 in inserter device arrangement 10, or positioned in another such device. The operator of this device with this interconnection lead 10$^{iv}$ provided therein can then cause, once this lead is positioned by the inserter device arrangement 10 used therewith against the same biological object with its outer layer portion removed, to be rotated to force helical lead 59 into engagement with that object.

Although the present invention has been described with reference to preferred embodiments, workers skilled in the art will recognize that changes may be made in form and detail without departing from the spirit and scope of the invention.

The invention claimed is:

1. A controlled relative motion system permitting a controlled motion member therein, joined to a base member therein, to selectively move with respect to that base member, said system comprising:
   a base support;
   a manipulable support;
   a plurality of doubled pivoting links each having therein a base link and a manipulable link rotatably coupled to one another by a link hinge supported both by said base link and said manipulable link, said base link in each of said plurality of doubled pivoting links being rotatably coupled to said base support by a base hinge supported both by said base link and said base support so as to be rotatable about a corresponding base link axis, and said manipulable link in each of said plurality of doubled pivoting links being rotatably coupled to said manipulable support by a manipulable hinge supported both by said manipulable link and said manipulable support so as to be rotatable about a corresponding support link axis; and
   a plurality of force imparting members spaced apart from one another, each positioned to have at least a part thereof across from one another extending in a common direction within a supporting structure having a unitary wall therein provided completely surrounding all of said parts of said force imparting members in a plane perpendicular to said common direction with said unitary wall extending along said parts of said force imparting members therein parallel thereto such that said manipulable support is positioned outside said supporting structure adjacent an end thereof, and at least one of said force imparting members in said plurality thereof being coupled to said base link in one of said plurality of doubled pivoting links so that repositionings of at least portions of that force imparting member within said supporting structure in said common direction forces that said base link to rotate about its corresponding said base link axis, and another of said plurality of force imparting members being coupled to said base support so that repositionings of at least portion of that force imparting member within said supporting structure in said common direction forces said base support to move toward or away from both at least a portion of that said force imparting member and said end of said supporting structure without repositioning in said common direction of said one of said plurality of force imparting members coupled to a said base link.

2. The apparatus of claim 1 wherein both said base link and said manipulable link in each of said plurality of doubled pivoting links are formed from, and joined together by, a common material, and said link hinge is formed at least in part by a thinned portion of that said material extending between said base link and said manipulable link in each of said plurality of doubled pivoting links.

3. The apparatus of claim 1 wherein both said base support and said base link in each of said plurality of doubled pivoting links are formed from, and joined together by, a common material, and said base hinge is formed at least in part by a thinned portion of that said material extending between said base support and said base link in each of said plurality of doubled pivoting links.

4. The apparatus of claim 1 wherein both said manipulable support and said manipulable link in each of said plurality of doubled pivoting links are formed from, and joined together by, a common material, and said manipulable hinge is formed at least in part by a thinned portion of that said material extending between said manipulable support and said manipulable link in each of said plurality of doubled pivoting links.

5. The apparatus of claim 1 wherein that one of said plurality of force imparting members coupled to a said base link in one of said plurality of doubled pivoting links has that portion thereof adjacent that said base link and that said base link both formed from, and joined together by, a common material in a forcing hinge, and said forcing hinge is formed at least in part by a thinned portion of that said material extending between that one of said plurality of force imparting member and said base link in each of said plurality of doubled pivoting links so coupled thereto.

6. The apparatus of claim 1 wherein that one of said plurality of force imparting members coupled to a said base link in one of said plurality of doubled pivoting links is a first angular positioning force imparting member, and another of said plurality of force imparting members as a second angular positioning force imparting member is coupled to a said base link in another of said plurality of doubled pivoting links differing from that to which said first angular positioning force imparting member is coupled.

7. The apparatus of claim 1 wherein said base support is an insertion base support, said base hinge is an insertion base hinge, said manipulable support is an insertion manipulable support, said manipulable hinge is an insertion manipulable hinge, and said plurality of doubled pivoting links is a plurality of insertion doubled pivoting links all together comprising an insertion joint with each of said insertion plurality of doubled pivoting links having an insertion base link and an insertion manipulable link rotatably coupled to one another by an insertion link hinge supported both by said insertion base link and said insertion manipulable link, and wherein that one of said plurality of force imparting members coupled to said insertion base link in one of said insertion plurality of doubled pivoting links comprises an oblong coupling shaft coupled at one end thereof to that said insertion base link and coupled at an opposite end thereof to a control joint of which that one of said plurality of force imparting members coupled to said insertion base link is further comprised.

8. The apparatus of claim 7 wherein said control joint further comprises a control base support, a control manipulable support, and a plurality of control doubled pivoting links each having therein a control base link and a control manipulable link rotatably coupled to one another by a control link hinge supported both by said control base link and said control manipulable link, said control base link in each of said plurality of control doubled pivoting links being rotatably coupled to said control base support by a control base hinge supported both by said control base link and said control base support so as to be rotatable about a corresponding control base link axis, and said control manipulable link in each of said control plurality of doubled pivoting links being rotatably coupled to said control manipulable support by a control manipulable hinge supported both by said control manipulable link and said control manipulable support so as to be rotatable about a corresponding control support link axis, and further wherein both said insertion base link and said insertion manipulable link in each of said plurality of insertion doubled pivoting links are formed from, and joined together by, a common material, and said insertion link hinge is formed at least in part by a thinned portion of that said material extending between said insertion base link and said insertion manipulable link in each of said plurality of insertion doubled pivoting links, and also wherein both said control base link and said control manipulable link in each of said plurality of control doubled pivoting links are formed from, and joined together by, a common material, and said control link hinge is formed at least in part by a thinned portion of that said material extending between said control base link and said control manipulable link in each of said plurality of control doubled pivoting links.

9. The apparatus of claim 8 wherein both said insertion base support and said insertion base link in each of said plurality of insertion doubled pivoting links are formed from, and joined together by, a common material, and said insertion base hinge is formed at least in part by a thinned portion of that said material extending between said insertion base support and said insertion base link in each of said plurality of insertion doubled pivoting links, and further wherein both said control base support and said control base link in each of said plurality of control doubled pivoting links are formed from, and joined together by, a common material, and said control base hinge is formed at least in part by a thinned portion of that said material extending between said control base support and said control base link in each of said plurality of control doubled pivoting links.

10. The apparatus of claim 8 wherein both said insertion manipulable support and said insertion manipulable link in each of said plurality of insertion doubled pivoting links are formed from, and joined together by, a common material, and said insertion manipulable hinge is formed at least in part by a thinned portion of that said material extending between said insertion manipulable support and said insertion manipulable link in each of said plurality of insertion doubled pivoting links, and further wherein both said control manipulable support and said control manipulable link in each of said plurality of control doubled pivoting links are formed from, and joined together by, a common material, and said control manipulable hinge is formed at least in part by a thinned portion of that said material extending between said control manipulable support and said control manipulable link in each of said plurality of control doubled pivoting links.

11. The apparatus of claim 8 wherein said oblong coupling shaft coupled at one end thereof to a said insertion base link has a coupling structure with that portion thereof adjacent that said insertion base link and that said insertion base link both formed from, and joined together by, a common material in a forcing hinge, and said forcing hinge is formed at least in part by a thinned portion of that said material extending between that adjacent said coupling structure portion and that said insertion base link.

12. The apparatus of claim 7 wherein that one of said plurality of force imparting members coupled to a said insertion base link in one of said plurality of insertion doubled pivoting links, comprises said coupling shaft as a first coupling shaft that is coupled at one end thereof to that said insertion base link, as a first positioning force imparting member, and further comprises another of said plurality of force imparting members as a second positioning force imparting member comprising an oblong second coupling shaft coupled at one end thereof to a said insertion base link in another of said plurality of insertion doubled pivoting links differing from that to which said first positioning force imparting member is coupled and is coupled at an opposite end thereof to said control joint of which second positioning force imparting member is further comprised.

13. The apparatus of claim 12 further comprising a separator having an oblong separator cylindrical shell with an open interior therein along its primary extent, said separator cylindrical shell having two recesses in an exterior side thereof extending along said primary extent thereof separated from one another by a shell lobe therebetween also extending along said primary extent of said separator cylindrical shell, and with said first and second coupling shafts each positioned in a corresponding one of said recesses.

14. The apparatus of claim 13 wherein that one of said plurality of force imparting members coupled to a said insertion base support comprises an activator slider, slidable along a sliding axis through said insertion base support but prevented from rotating thereabout, and positioned at least partly about said first and second coupling shafts in being coupled to said separator that is slidable along said sliding axis and rotatable thereabout, and further, is coupled to said insertion base support.

15. The apparatus of claim 14 further comprising a coupling member in said activator slider that is rotatable therein about said sliding axis with said separator being coupled to said coupling member.

16. The apparatus of claim 15 further comprising a slide support along at least a portion of which said separator can be slid, said slide support being coupled to said control base support.

17. The apparatus of claim 16 further comprising said supporting structure being a barrel formed substantially as a cylindrical shell and positioned within said activator slider and said coupling member and about said base support slider and said slide support.

18. The apparatus of claim 17 wherein said barrel also is positioned about at least a portion of said insertion base support and at least a portion of said control base support.

19. The apparatus of claim 18 wherein said barrel is supported on a handle so as to be rotatable with respect thereto.

20. The apparatus of claim 12 further comprising said supporting structure being a barrel formed substantially as a cylindrical shell and positioned about said first and second coupling shafts.

21. The apparatus of claim 20 wherein said barrel also is positioned about at least a portion of said insertion base support and at least a portion of said control base support.

22. The apparatus of claim 21 wherein said barrel is supported on a handle so as to be rotatable with respect thereto.

23. The apparatus of claim 7 further comprising said supporting structure being a barrel formed substantially as a cylindrical shell and positioned about said coupling shaft.

24. The apparatus of claim 23 wherein said barrel also is positioned about at least a portion of said insertion base support and at least a portion of said control joint.

25. The apparatus of claim 24 wherein said barrel is supported on a handle so as to be rotatable with respect thereto.

26. The apparatus of claim 1 wherein that one of said plurality of force imparting members coupled to a said base support comprises an activator slider, slidable along and rotatable about a sliding axis through said base support but prevented from rotating with respect to said base support, coupled to a base support slider that is slidable along said sliding axis and rotatable thereabout.

27. The apparatus of claim 26 further comprising a coupling member in said activator slider that is rotatable therein about said sliding axis and to which both said activator slider and said base support slider are slidably and rotatably coupled.

28. The apparatus of claim 27 further comprising a slide support along at least a portion of which said base support slider can be slid.

29. The apparatus of claim 28 further comprising said supporting structure being a barrel formed substantially as a cylindrical shell and positioned within said activator slider and said coupling member and about said base support slider and said slide support.

30. The apparatus of claim 1 wherein said barrel is supported on a handle so as to be rotatable with respect thereto.

\* \* \* \* \*

UNITED STATES PATENT AND TRADEMARK OFFICE
CERTIFICATE OF CORRECTION

| | |
|---|---|
| PATENT NO. | : 8,197,469 B2 |
| APPLICATION NO. | : 10/760898 |
| DATED | : June 12, 2012 |
| INVENTOR(S) | : Mark E. Rosheim |

It is certified that error appears in the above-identified patent and that said Letters Patent is hereby corrected as shown below:

In the Specification

Col. 3, Line 20
 Delete "thereofwhich"
 Insert --thereof which--

Col. 6, Line 36
 Delete "31 con"
 Insert --31con--

Col. 7, Line 41
 Delete "aims"
 Insert --arms--

Col. 8, Line 37
 Delete "ofthe"
 Insert --of the--

Col. 15, Line 10
 Delete "there against"
 Insert --thereagainst--

In the Claims

Col. 15, Line 63
 Insert --a-- before "said base link"

Signed and Sealed this
Twenty-sixth Day of November, 2013

Margaret A. Focarino
*Commissioner for Patents of the United States Patent and Trademark Office*